US012653789B2

(12) United States Patent
Nunes et al.

(10) Patent No.: US 12,653,789 B2
(45) Date of Patent: Jun. 16, 2026

(54) ADAGRASIB SOLID PHARMACEUTICAL COMPOSITIONS

(71) Applicant: MIRATI THERAPEUTICS, INC., Princeton, NJ (US)

(72) Inventors: Cletus Nunes, San Diego, CA (US); Mehrdad Kheiripour, San Diego, CA (US); Monika Gavireddi, San Diego, CA (US)

(73) Assignee: MIRATI THERAPEUTICS, INC., Princeton, NJ (US)

( * ) Notice: Subject to any disclaimer, the term of this patent is extended or adjusted under 35 U.S.C. 154(b) by 0 days.

(21) Appl. No.: 18/784,276

(22) Filed: Jul. 25, 2024

(65) Prior Publication Data

US 2024/0374525 A1 Nov. 14, 2024

Related U.S. Application Data

(63) Continuation of application No. PCT/US2023/030689, filed on Aug. 21, 2023.

(60) Provisional application No. 63/400,640, filed on Aug. 24, 2022, provisional application No. 63/399,619, filed on Aug. 19, 2022.

(51) Int. Cl.

| | |
|---|---|
| ***A61K 9/20*** | (2006.01) |
| ***A61K 9/00*** | (2006.01) |
| ***A61K 9/28*** | (2006.01) |
| ***A61K 31/519*** | (2006.01) |

(52) U.S. Cl.

CPC .......... *A61K 9/2054* (2013.01); *A61K 9/0053* (2013.01); *A61K 9/2009* (2013.01); *A61K 9/2013* (2013.01); *A61K 9/2018* (2013.01); *A61K 9/2027* (2013.01); *A61K 9/28* (2013.01); *A61K 31/519* (2013.01)

(58) Field of Classification Search

None

See application file for complete search history.

(56) References Cited

U.S. PATENT DOCUMENTS

| | | | | |
|---|---|---|---|---|
| 10,689,377 B2 | 6/2020 | Blake et al. | | |
| 2005/0051922 A1 | 3/2005 | Nangia et al. | | |
| 2010/0310651 A1 | 12/2010 | Mittal | | |
| 2015/0196493 A1 | 7/2015 | Szymczak et al. | | |
| 2019/0224175 A1 | 7/2019 | Golden et al. | | |
| 2020/0360374 A1* | 11/2020 | Henary | ................ | A61K 31/505 |
| 2021/0113569 A1* | 4/2021 | Goncalves | ........... | A61K 9/2009 |
| 2022/0395507 A1* | 12/2022 | Haling | .................... | A61P 35/00 |

FOREIGN PATENT DOCUMENTS

| | | | | | |
|---|---|---|---|---|---|
| CA | 3201612 | A1 * | 6/2022 | ......... | A61K 31/4709 |
| CN | 115521312 | A | 12/2022 | | |
| EP | 3628664 | A1 * | 4/2020 | | |
| WO | 2019099524 | A1 | 5/2019 | | |
| WO | WO-2022056307 | A1 * | 3/2022 | ........... | A61K 31/519 |

OTHER PUBLICATIONS

International Search Report and Written Opinion for PCT Application No. PCT/US2023/030689, mailed on Feb. 26, 2024, 12 pages.
P01116 • Rask_Human, UniProtKB/Swiss-Prot, Retrieved on Aug. 27, 2024, 14 pages.
Alamgeer et al., "Novel Therapeutic Targets in Non-small Cell Lung Cancer", Curr Opin Pharmacol., 2013, 13(3):394-401.
Berge et al., "Pharmaceutical Salts", Journal of Pharmaceutical Sciences, Jan. 1977, 66(1):1-19.
Dogan et al., "Molecular Epidemiology of EGFR and KRAS Mutations in 3,026 Lung Adenocarcinomas: Higher Susceptibility of Women to Smoking-related Kras-mutant Cancers", Clin Cancer Res., 2012, 18(22):6169-6177.
Fell et al., "Identification of the Clinical Development Candidate MRTX849, a Covalent KRASG12C Inhibitor for the Treatment of Cancer", Journal of Medicinal Chemistry, 2020, 63(13): 6679-6693.
Mccormick, Frank, "KRAS as a Therapeutic Target", Clin Cancer Res., 2015, 21(8):1797-1801.
Ostrem et al., "K-Ras(G12C) Inhibitors Allosterically Control GTP Affinity and Effector Interactions", Nature, 2013, 503(7477):548-551.
Samatar et al., "Targeting RAS-ERK Signalling in Cancer: Promises and Challenges", Nat Rev Drug Discov., 2014, 13(12):928-942.
Santos et al., "Malignant Activation of a K-Ras Oncogene in Lung Carcinoma but Not in Normal Tissue of the Same Patient", Science, 1984, 223(4637):661-664.
International Preliminary Report on Patentability for PCT Application No. PCT/US2023/030689; Dated Mar. 6, 2025; 9 pgs.

* cited by examiner

*Primary Examiner* — Susan T Tran
(74) *Attorney, Agent, or Firm* — Mintz, Levin, Cohn, Ferris, Glovsky and Popeo, P.C.

(57) ABSTRACT

Pharmaceutical compositions in solid form comprising adagrasib, suitable for oral dosage to treat subjects having cancer; as well as methods of manufacturing the compositions, and methods of treating cancer.

9 Claims, 1 Drawing Sheet

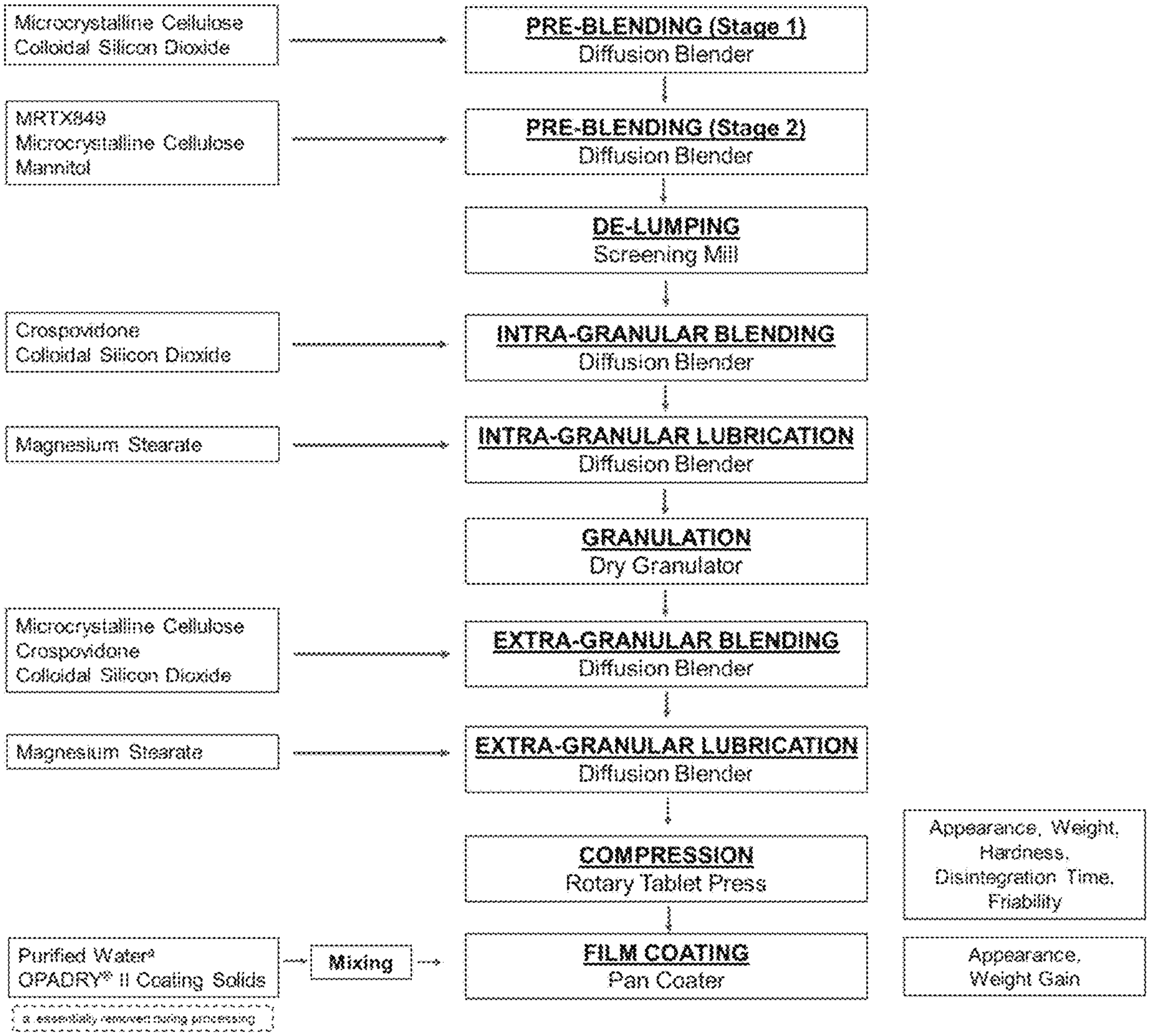

Microcrystalline Cellulose
Colloidal Silicon Dioxide
PRE-BLENDING (Stage 1)
Diffusion Blender
MRTX849
Microcrystalline Cellulose
Mannitol
PRE-BLENDING (Stage 2)
Diffusion Blender
DE-LUMPING
Screening Mill
Crospovidone
Colloidal Silicon Dioxide
INTRA-GRANULAR BLENDING
Diffusion Blender
Magnesium Stearate
INTRA-GRANULAR LUBRICATION
Diffusion Blender
GRANULATION
Dry Granulator
Microcrystalline Cellulose
Crospovidone
Colloidal Silicon Dioxide
EXTRA-GRANULAR BLENDING
Diffusion Blender
Magnesium Stearate
EXTRA-GRANULAR LUBRICATION
Diffusion Blender
COMPRESSION
Rotary Tablet Press
Appearance, Weight, Hardness, Disintegration Time, Friability
Purified Water[a]
OPADRY® II Coating Solids
Mixing
FILM COATING
Pan Coater
Appearance, Weight Gain
a: essentially removed during processing

ADAGRASIB SOLID PHARMACEUTICAL COMPOSITIONS

FIELD OF THE INVENTION

The present invention generally relates to solid pharmaceutical compositions of adagrasib (2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl) piperazin-2-yl|acetonitrile); methods for preparing these compositions, and methods of their use for the treatment of various diseases and disorders.

BACKGROUND OF THE INVENTION

Kirsten Rat Sarcoma 2 Viral Oncogene Homolog ("KRas") is a small GTPase and a member of the Ras family of oncogenes. KRas serves as a molecular switch cycling between inactive (GDP-bound) and active (GTP-bound) states to transduce upstream cellular signals received from multiple tyrosine kinases to downstream effectors regulating a wide variety of processes, including cellular proliferation (e.g., see Alamgeer et al., (2013) Current Opin Pharmcol. 13:394-401).

The role of activated KRas in malignancy was observed over thirty years ago (e.g., see Santos et al., (1984) Science 223:661-664). Aberrant expression of KRas accounts for up to 20% of all cancers and oncogenic KRas mutations that stabilize GTP binding and lead to constitutive activation of KRas and downstream signaling have been reported in 25-30% of lung adenocarcinomas. (e.g., see Samatar and Poulikakos (2014) Nat Rev Drug Disc 13 (12): 928-942 doi: 10.1038/nrd428). Single nucleotide substitutions that result in missense mutations at codons 12 and 13 of the KRas primary amino acid sequence comprise approximately 40% of these KRas driver mutations in lung adenocarcinoma, with a G12C transversion being the most common activating mutation (e.g., see Dogan et al., (2012) Clin Cancer Res. 18 (22): 6169-6177, published online 2012 Sep. 26. doi: 10.1158/1078-0432.CCR-11-3265).

The well-known role of KRas in malignancy and the discovery of these frequent mutations in KRas in various tumor types made KRas a highly attractable target of the pharmaceutical industry for cancer therapy. Notwithstanding thirty years of large scale discovery efforts to develop inhibitors of KRas for treating cancer, no KRas inhibitor has demonstrated sufficient safety and/or efficacy to obtain regulatory approval (e.g., see McCormick (2015) Clin Cancer Res. 21 (8): 1797-1801).

Recently, irreversible, covalent inhibitors that target KRas G12C have been described (e.g., see Ostrem et al., (2013) Nature 503:548-551). For instance, commonly-owned and assigned U.S. Provisional Application Ser. No. 62/586,775 discloses potent, orally bioavailable compounds that irreversibly bind to KRas G12C for treating KRas G12C-mediated cancers.

A covalent, irreversible inhibitor of KRas G12C is adagrasib (2-[(2S)-4-[7-(8-chloro-1-naphthyl)-2-[[(2S)-1-methylpyrrolidin-2-yl|methoxy]-6,8-dihydro-5H-pyrido[3,4-d] pyrimidin-4-yl]-1-(2-fluoroprop-2-enoyl) piperazin-2-yl|acetonitrile), also known as MRTX849. An amorphous form of this compound was described in International Patent Application PCT/US2018/061060 filed Nov. 14, 2018, published as WO2019/099524A1 on May 23, 2019 at Example 478, and in Fell et al., (2020) J.Med. Chem. 63, 6679-6693. A crystalline form of this compound was described in International Patent Application PCT/US2021/049940 filed Sep. 10, 2021, published as WO2022/056307 on Mar. 17, 2022.

Furthermore, it is desirable to reduce adverse events (AE) (also known as side effects) such as nausea, vomiting, diarrhea when the formulations are administered to patients.

A need therefore exists for a pharmaceutical composition of adagrasib which displays suitable bioavailability and shelf-life stability, which is not susceptible to liquid capsule leakage over time, and which has fewer side effects compared with capsule formulations.

SUMMARY OF THE INVENTION

In one embodiment, the present invention provides a pharmaceutical composition, in solid form, suitable for oral administration to a subject, including but not limited to a human subject, which comprises adagrasib or a salt thereof, wherein the solid pharmaceutical composition, after administration to the subject, is capable of providing AUC $_{0\rightarrow\infty}$ (the area under the curve of a plot of plasma drug concentration versus time) for adagrasib of at least, or about, 12000 ng*hr/mL under fasted conditions and/or of at least, or about, 19000 ng*hr/mL under fed conditions.

In another embodiment, the solid pharmaceutical composition, after administration to a subject, is capable of providing AUC $_{0\rightarrow last}$ for adagrasib of at least, or about, 12000 ng*hr/mL under fasted conditions and/or of at least, or about, 19000 ng*hr/mL under fed conditions.

In another embodiment, the solid pharmaceutical composition, after administration to a subject, is capable of providing $C_{max}$ for the compound of formula (I) of at least, or about, 480 ng/ml under fasted conditions and/or of at least, or about, 630 ng/mL under fed conditions.

In another embodiment, the solid pharmaceutical composition, after administration to a subject, is capable of providing: a) AUC $_{0\rightarrow\infty}$ for adagrasib of at least, or about, 12000 ng*hr/mL under fasted conditions and/or of at least, or about, 19000 ng*hr/mL under fed conditions; b) AUC $_{0\rightarrow last}$ for adagrasib of at least, or about, 12000 ng*hr/mL under fasted conditions and/or of at least, or about, 19000 ng*hr/mL under fed conditions; and c) $C_{max}$ for adagrasib of at least, or about, 480 ng/mL under fasted conditions and/or of at least, or about, 630 ng/ml under fed conditions.

In another embodiment, the solid pharmaceutical composition provides a $T_{max}$ of less than about 6.5 hours, and preferably between about 6.0-6.25 hours.

In any of the embodiments, it is not required that the recited pharmacokinetic (PK) values, such as AUC $_{0\rightarrow\infty}$, AUC $_{0\rightarrow last}$, and $C_{max}$, are achieved by administering a single pharmaceutical composition. The invention contemplates, and explicitly includes, embodiments where these PK values are achieved following administration of several solid pharmaceutical compositions as a single dose (e.g., if a solid pharmaceutical composition (e.g., a tablet) comprises 200 mg adagrasib, the single dose may include, for example, three of such pharmaceutical compositions, for the total administered amount of 600 mg adagrasib).

In another embodiment, adagrasib is present as a salt thereof.

In another embodiment, the solid pharmaceutical composition comprises at least one additional anticancer compound in addition to the adagrasib.

In another embodiment, the solid pharmaceutical composition is in the form of a powder or a tablet, including an encapsulated powder.

In another embodiment, the solid pharmaceutical composition is in the form of a tablet.

In another embodiment, the tablet of the invention comprises a film coat.

In another embodiment, the tablet of the invention comprises: adagrasib, one or more diluents, a disintegrant, a glidant, a lubricant, and a film coat.

In a preferred embodiment, the diluent is selected from the group consisting of microcrystalline cellulose, mannitol, and combinations thereof.

In another preferred embodiment, the disintegrant comprises crospovidone.

In another preferred embodiment, the glidant comprises colloidal silicon dioxide.

In another preferred embodiment, the lubricant comprises magnesium stearate.

In a preferred embodiment, the tablet of the invention comprises adagrasib, microcrystalline cellulose, mannitol, crospovidone, colloidal silicon dioxide, magnesium stearate and a film coat.

In another embodiment, the solid pharmaceutical composition is provided as a unit dosage form.

In one embodiment, the amount of adagrasib in the solid pharmaceutical composition is at least, or about, 200 mg.

In another embodiment, the amount of adagrasib in the solid pharmaceutical composition is at least, or about, 300 mg.

In another embodiment, the amount of adagrasib in the solid pharmaceutical composition is at least, or about, 400 mg.

In another embodiment, the amount of adagrasib in the solid pharmaceutical composition is at least, or about, 600 mg.

In another embodiment, the composition is in the form of a tablet and comprises:

(1) adagrasib constituting about 30-35% percent of the composition;

(2) microcrystalline cellulose constituting about 50-55% of the composition;

(3) mannitol constituting about 8-10% of the composition;

(4) crospovidone constituting about 2% to about 5% of the composition;

(5) colloidal silicon dioxide constituting up to about 0.5-1.5% of the composition; and (6) magnesium stearate constituting about 1-2% of the composition, wherein all percentages are percentages by weight and wherein the total weight is 100%.

In another embodiment, the composition further comprises a film coat.

In another embodiment, the composition is in the form of a tablet and comprises: (1) adagrasib constituting about 30-67% percent of the composition;

(2) microcrystalline cellulose constituting about 20-55% of the composition;

(3) mannitol constituting about 0-10% of the composition;

(4) crospovidone constituting about 2% to about 5% of the composition;

(5) colloidal silicon dioxide constituting up to about 0.5-2% of the composition; and (6) magnesium stearate constituting about 1-3% of the composition.

wherein all percentages are percentages by weight and wherein the total weight is 100%.

In another embodiment, the composition is in the form of a tablet and comprises:

(1) adagrasib constituting about 50-67% percent of the composition;

(2) microcrystalline cellulose constituting about 20-45% of the composition;

(3) mannitol constituting about 0-10% of the composition;

(4) crospovidone constituting about 2% to about 5% of the composition;

(5) colloidal silicon dioxide constituting up to about 0.5-2% of the composition; and (6) magnesium stearate constituting about 1-3% of the composition.

wherein all percentages are percentages by weight and wherein the total weight is 100%.

In a preferred embodiment, the composition of the invention comprises:

(1) adagrasib at about 33.3% percent of the composition;

(2) microcrystalline cellulose at about 51.2% of the composition;

(3) mannitol at about 10.0% of the composition;

(4) crospovidone at about 3.0% of the composition;

(5) colloidal silicon dioxide at about 1.0% of the composition; and (6) magnesium stearate at about 1.5% of the composition, wherein all percentages are percentages by weight and wherein the total weight is 100%.

In another embodiment, the solid pharmaceutical composition is prepared by a process which comprises the steps of:

(a) pre-blending, wherein diluents, a glidant, and adagrasib are blended together;

(b) de-lumping the components of step (a) using a screening mill;

(c) blending the components of step (b) with a disintegrant, and a glidant;

(d) lubricating by adding a lubricant to the components of step (c);

(e) performing a dry granulation of the components of step (d) using a roller compactor, producing a granulated blend;

(f) blending a diluent, a disintegrant and a glidant with the granulated blend of step (e);

(g) lubricating by adding a lubricant to the components of step (f) to produce a lubricated blend;

(h) performing compression by charging the lubricated blend of step (g) to a rotary tablet press and compressing the lubricated blend into core tablets; and (i) performing film coating by charging the core tablets of step (h) into a pan coater and adding a film coating agent.

One or more pharmaceutically acceptable excipients (or combinations thereof) may be included as intra-granular material, i.e., included prior to conducting dry granulation; and/or such excipients may be added as extra-granular material to the dry granulation product, i.e., added after the dry granulation product has been made.

In yet another embodiment, the invention is directed to a method of making a solid pharmaceutical composition comprising adagrasib or a salt thereof, wherein said solid pharmaceutical composition is made by dry granulation.

In one embodiment, the method comprises the steps of:

(a) pre-blending, wherein a diluent, a glidant, and adagrasib are blended together;

(b) de-lumping the components of step (a) using a screening mill;

(c) blending the components of step (b) with a disintegrant, and a glidant;

(d) lubricating by adding a lubricant to the components of step (c);

(e) performing a dry granulation of the components of step (d) using a roller compactor, producing a granulated blend;

(f) blending a diluent, a disintegrant and a glidant with the granulated blend of step (e);

(g) lubricating by adding a lubricant to the components of step (f) to produce a lubricated blend;

(h) performing compression by charging the lubricated blend of step (g) to a rotary tablet press and compressing the lubricated blend into tablet cores; and (i) performing film coating by charging the core tablets of step (h) into a pan coater and adding a film coating agent.

In one embodiment, the solid pharmaceutical composition (e.g., tablet) may comprise additional excipients selected from the group consisting of diluents, fillers, super-disintegrants, binders, glidants, lubricants, and combinations thereof.

In another embodiment, the invention is directed to a method of treating cancer in a subject in need thereof, comprising administering to the subject a therapeutically effective amount of the solid pharmaceutical composition of the present invention. In one embodiment, the therapeutically effective amount is at least, or about, 600 mg of adagrasib. In one embodiment, the cancer is a KRas G12C-associated cancer. In one embodiment, the KRas G12C-associated cancer is lung cancer. In one embodiment, the solid pharmaceutical composition is a tablet.

Also provided herein are methods for treating cancer in a subject in need thereof, the method comprising (a) determining that cancer is associated with a KRas G12C mutation (e.g., a KRas G12C-associated cancer) (e.g., as determined using a regulatory agency-approved, e.g., FDA-approved, assay or kit); and (b) administering to the patient a therapeutically effective amount of the solid pharmaceutical composition of the present invention. In one embodiment, the solid pharmaceutical composition is a tablet.

In one embodiment, the provided methods of treating cancer cause fewer side effects in the subject than side effects associated with administering a capsule composition of the same amount of adagrasib.

BRIEF DESCRIPTION OF THE DRAWINGS

FIG. 1 is a manufacturing process flow diagram depicting one way of making solid pharmaceutical compositions of the invention.

DETAILED DESCRIPTION OF THE INVENTION

Definitions

The term "adagrasib" as used herein refers to a compound with the following formula:

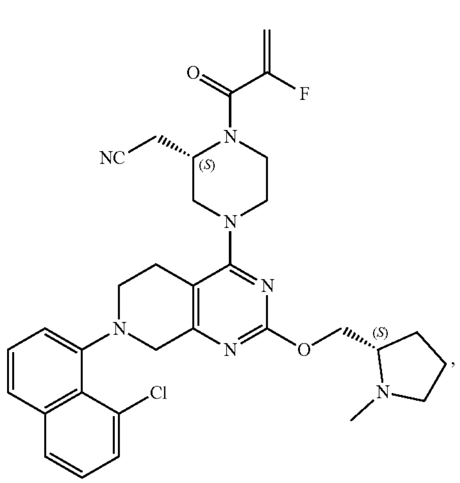

as well as pharmaceutically acceptable salts of this compound. The compound has the following chemical name: (2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl) piperazin-2-yl]acetonitrile). It is also known as MRTX849. The invention encompasses amorphous and crystalline forms of adagrasib. An amorphous form of this compound was described in International Patent Application PCT/US2018/061060 filed Nov. 14, 2018, published as WO2019/099524A1 on May 23, 2019 at Example 478, and in Fell et al., (2020) J.Med. Chem. 63, 6679-6693. A crystalline form of this compound was described in International Patent Application PCT/US2021/049940 filed Sep. 10, 2021, published as WO2022/056307 on Mar. 17, 2022. Form 1, as referred to in this application, corresponds to Form A in PCT/US2021/049940; Form 2, as referred to in this application, corresponds to Form B in PCT/US2021/049940. The tablets described herein preferably comprise crystalline form(s) of adagrasib. The contents of these patent applications and of the literature reference are hereby incorporated by reference in their entirety.

As used herein, "KRas G12C" refers to a mutant form of a mammalian KRas protein that contains an amino acid substitution of a cysteine for a glycine at amino acid position 12. The assignment of amino acid codon and residue positions for human KRas is based on the amino acid sequence identified by UniProtKB/Swiss-Prot P01116: Variant p.Glyl2Cys.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant the diluent, excipient or carrier must be compatible with the other ingredients of the formulation and not deleterious to the recipient thereof.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "solid forms" and related terms used herein, unless otherwise specified, refers to crystalline forms comprising adagrasib and its various salt forms.

The term "crystalline" and related terms used herein, when used to describe a substance, component or product, means that the substance, component or product is crystalline as determined by X-ray diffraction. See, for example, *Remington's Pharmaceutical Sciences,* $18^{th}$ *ed*., Mack Publishing, Easton PA, p. 173 (1990); *The United States Pharmacopeia,* $23^{rd}$ *ed*., pp. 1843-1844 (1995); the contents of which are hereby incorporated by reference in their entireties.

The term "crystalline forms" and related terms herein refers to the various crystalline modifications of a given substance, including, but not limited to, polymorphs, solvates, hydrates, co-crystals and other molecular complexes, as well as salts, solvates of salts, hydrates of salts, other molecular complexes of salts, and polymorphs thereof.

The term "pharmaceutically acceptable salts" is meant to include salts of active compounds which are prepared with relatively nontoxic acids. Acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic; propionic; isobutyric; maleic; malonic; benzoic; succinic; suberic; fumaric; mandelic; phthalic; benzenesulfonic; toluenesulfonic, including p-toluenesulfonic, m-toluenesulfonic, and o-toluenesulfonic; citric; tartaric; methanesulfonic; and the like. Also included are salts of amino acids such as arginate and the like, and salts of organic acids like glucuronic or galactunoric acids and the like (see, for example, Berge et al. J. Pharm. Sci. 66:1-19 (1977)).

The term, "amorphous form," as used herein, refers to a noncrystalline form of a substance.

The terms, "polymorphs" and "polymorphic forms" and related terms herein refer to crystal forms of a molecule. Different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in bioavailability). Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

Techniques for characterizing polymorphs include, but are not limited to, differential scanning calorimetry (DSC), X-ray powder diffractometry (XRPD), single crystal X-ray diffractometry, vibrational spectroscopy, e.g., IR and Raman spectroscopy, solid state NMR, hot stage optical microscopy, scanning electron microscopy (SEM), electron crystallography and quantitative analysis, particle size analysis (PSA), surface area analysis, solubility studies and dissolution studies.

The term, "solvate," as used herein, refers to a crystal form of a substance which contains solvent. The term "hydrate" refers to a solvate wherein the solvent is water.

The term, "desolvated solvate," as used herein, refers to a crystal form of a substance which can only be made by removing the solvent from a solvate.

The term "excipient" refers to an inactive ingredient of the pharmaceutical compositions of the invention. It includes, but is not limited to, solvents, wetting agents, diluents, superdisintegrants, binders, glidants, and lubricants.

The terms "treat", "treating" or "treatment", as used herein, refer to the reduction or amelioration of the progression, severity, and/or duration of a disorder or the eradication, reduction or amelioration of symptoms of a disorder, or the delay of the recurrence or onset of a disorder or one or more symptoms thereof in a subject that results from the administration of one or more compound.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having a KRas G12C mutation (e.g., as determined using a regulatory agency-approved, e.g., FDA-approved, assay or kit). In some embodiments, the subject has a tumor that is positive for a KRas G12C mutation (e.g., as determined using a regulatory agency-approved assay or kit). The subject can be a subject with a tumor(s) that is positive for a KRas G12C mutation (e.g., identified as positive using a regulatory agency-approved, e.g., FDA-approved, assay or kit). The subject can be a subject whose tumors have a KRas G12C mutation (e.g., where the tumor is identified as such using a regulatory agency-approved, e.g., FDA-approved, kit or assay). In some embodiments, the subject is suspected of having a KRas G12C gene-associated cancer. In some embodiments, the subject has a clinical record indicating that the subject has a tumor that has a KRas G12C mutation (and optionally the clinical record indicates that the subject should be treated with any of the compositions provided herein).

The term "pediatric patient" as used herein refers to a patient under the age of 16 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson Textbook of Pediatrics, 15th Ed. Philadelphia: W. B. Saunders Company, 1996; Rudolph A M, et al. Rudolph's Pediatrics, 21st Ed. New York: McGraw-Hill, 2002; and Avery M D, First L R. Pediatric Medicine, 2nd Ed. Baltimore: Williams & Wilkins; 1994.

In some embodiments of any of the methods or uses described herein, an assay is used to determine whether the patient has KRas G12C mutation using a sample (e.g., a biological sample or a biopsy sample such as a paraffin-embedded biopsy sample) from a patient (e.g., a patient suspected of having a KRas G12C-associated cancer, a patient having one or more symptoms of a KRas G12C-associated cancer, and/or a patient that has an increased risk of developing a KRas G12C-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR, quantitative real-time RT-PCR, allele-specific genotyping or ddPCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

As used herein, a "therapeutically effective amount" is an amount that is sufficient to ameliorate, or in some manner reduce a symptom or stop or reverse progression of a condition, or negatively modulate or inhibit the activity of KRas G12C. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

As used herein, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "fasted conditions" refers to a subject fasting at least 10 hours before being administered compositions of the invention.

The term "fed conditions" refers to a subject being administered compositions of the inventions no later than 30-45 minutes after consuming food.

The term, "AUC," as used herein, refers to the area under the curve of a plot of plasma drug concentration versus time.

The term, "$T_{max}$," as used herein, refers to the time after administration of a drug when the maximum plasma concentration is reached.

A "KRas G12C-associated disease or disorder" as used herein refers to diseases or disorders associated with or mediated by or having a KRas G12C mutation. A non-limiting example of a KRas G12C-associated disease or disorder is a KRas G12C-associated cancer.

DETAILED DESCRIPTION OF COMPOSITIONS AND METHODS

The present invention is based on a surprising discovery that solid pharmaceutical compositions (e.g., tablets) comprising adagrasib result in fewer adverse events (AEs, also referred to as "side effects"), such as nausea, vomiting, diarrhea, when administered to patients, than capsule formulations comprising the same amount of adagrasib. Without wishing to be bound to a specific theory, it is hypothesized that the lower number of the upper GI related AEs could be due to lower maximum concentration ($C_{max}$) compared to the capsules. Emerging data from the ongoing Phase 3 study indicate that the tablet administration also results in fewer upper GI AEs. Another possibility is that, in the case of the tablet, the disintegration mechanism and greater density may lead to more rapid clearance of the drug from the stomach. In contrast, the capsule may float or adhere to the stomach lining and rapidly release the drug in the stomach, leading to higher local drug levels. If the drug is irritating to stomach this could lead to higher AEs.

Thus, in one embodiment, the present invention provides a pharmaceutical composition, in solid form, suitable for oral administration to a subject, including but not limited to a human subject, which comprises adagrasib or a salt thereof, wherein the solid pharmaceutical composition, after administration to the subject, is capable of providing $AUC_{0\rightarrow\infty}$ (the area under the curve of a plot of plasma drug concentration versus time) for adagrasib of at least, or about, 12000 ng*hr/mL under fasted conditions and/or of at least, or about, 19000 ng*hr/mL under fed conditions.

In another embodiment, the solid pharmaceutical composition, after administration to a subject, is capable of providing $AUC_{0\rightarrow last}$ for adagrasib of at least, or about, 12000 ng*hr/mL under fasted conditions and/or of at least, or about, 19000 ng*hr/mL under fed conditions.

In another embodiment, the solid pharmaceutical composition, after administration to a subject, is capable of providing $C_{max}$ for the compound of formula (I) of at least, or about, 480 ng/ml under fasted conditions and/or of at least, or about, 630 ng/mL under fed conditions.

In another embodiment, the solid pharmaceutical composition, after administration to a subject, is capable of providing: a) $AUC_{0\rightarrow\infty}$ for adagrasib of at least, or about, 12000 ng*hr/mL under fasted conditions and/or of at least, or about, 19000 ng*hr/mL under fed conditions; b) $AUC_{0\rightarrow last}$ for adagrasib of at least, or about, 12000 ng*hr/mL under fasted conditions and/or of at least, or about, 19000 ng*hr/mL under fed conditions; and c) $C_{max}$ for adagrasib of at least, or about, 480 ng/ml under fasted conditions and/or of at least, or about, 630 ng/mL under fed conditions.

In another embodiment, the solid pharmaceutical composition provides a $T_{max}$ of less than about 6.5 hours, and preferably between about 6.0-6.25 hours.

In any of the embodiments, it is not required that the recited pharmacokinetic (PK) values, such as $AUC_{0\rightarrow\infty}$, $AUC_{0\rightarrow last}$, and $C_{max}$, are achieved by administering a single pharmaceutical composition. The invention contemplates, and explicitly includes, embodiments where these PK values are achieved following administration of several solid pharmaceutical compositions as a single dose (e.g., if a solid pharmaceutical composition (e.g., a tablet) comprises 200 mg adagrasib, the single dose may include, for example, three of such pharmaceutical compositions, for the total administered amount of 600 mg adagrasib).

In another embodiment, adagrasib is present as a salt thereof.

In another embodiment, the solid pharmaceutical composition comprises at least one additional anticancer compound in addition to the adagrasib.

In another embodiment, the solid pharmaceutical composition is in the form of a powder or a tablet, including an encapsulated powder.

In another embodiment, the solid pharmaceutical composition is in the form of a tablet.

In one embodiment, the solid pharmaceutical composition (e.g., tablet) may comprise various excipients selected from the group consisting of solvents, wetting agents, diluents, fillers, super-disintegrants, binders, glidants, lubricants, and combinations thereof. It should be understood that the invention contemplates use of other excipients that serve substantially the same functions in substantially the same manner as those described above.

Tablets may contain the solid active ingredient in admixture with at least one pharmaceutically acceptable excipient which is suitable for the manufacture of tablets. The excipient may be, for example; a disintegrating agent, such as a super-disintegrant; a binder; a diluent; a glidant; a lubricant; an emulsifier; or any other excipient known to one of skill in the art.

Preferred tablets are those which provide good potency, content uniformity, hardness, friability and dissolution, and which contribute to the chemical and physical stability of the pharmaceutical compositions.

In another embodiment, the tablet of the invention comprises a film coat.

In another embodiment, the tablet of the invention comprises: adagrasib, one or more diluents, a disintegrant, a glidant, a lubricant, and a film coat.

In a preferred embodiment, the diluent is selected from the group consisting of microcrystalline cellulose, mannitol, and combinations thereof.

In another preferred embodiment, the disintegrant comprises crospovidone.

In another preferred embodiment, the glidant comprises colloidal silicon dioxide.

In another preferred embodiment, the lubricant comprises magnesium stearate.

In a preferred embodiment, the tablet of the invention comprises adagrasib, microcrystalline cellulose, mannitol, crospovidone, colloidal silicon dioxide, magnesium stearate and a film coat.

In another embodiment, the solid pharmaceutical composition is provided as a unit dosage form.

In one embodiment, the amount of adagrasib in the solid pharmaceutical composition is at least, or about, 200 mg.

In another embodiment, the amount of adagrasib in the solid pharmaceutical composition is at least, or about, 300 mg.

In another embodiment, the amount of adagrasib in the solid pharmaceutical composition is at least, or about, 400 mg.

In another embodiment, the amount of adagrasib in the solid pharmaceutical composition is at least, or about, 600 mg.

In another embodiment, the composition is in the form of a tablet and comprises:

(1) adagrasib constituting about 30-35% percent of the composition;

(2) microcrystalline cellulose constituting about 50-55% of the composition;

(3) mannitol constituting about 8-10% of the composition;

(4) crospovidone constituting about 2% to about 5% of the composition;

(5) colloidal silicon dioxide constituting up to about 0.5-1.5% of the composition; and (6) magnesium stearate constituting about 1-2% of the composition, wherein all percentages are percentages by weight and wherein the total weight is 100%.

In another embodiment, the composition is in the form of a tablet and comprises:

(1) adagrasib constituting about 30-67% percent of the composition;

(2) microcrystalline cellulose constituting about 20-45% of the composition;

(3) mannitol constituting about 0-10% of the composition;

(4) crospovidone constituting about 2% to about 5% of the composition;

(5) colloidal silicon dioxide constituting up to about 0.5-2% of the composition; and (6) magnesium stearate constituting about 1-3% of the composition, wherein all percentages are percentages by weight and wherein the total weight is 100%.

In another embodiment, the composition is in the form of a tablet and comprises: (1) adagrasib constituting about 50-67% percent of the composition;

(2) microcrystalline cellulose constituting about 20-45% of the composition;

(3) mannitol constituting about 0-10% of the composition;

(4) crospovidone constituting about 2% to about 5% of the composition;

(5) colloidal silicon dioxide constituting up to about 0.5-2% of the composition; and (6) magnesium stearate constituting about 1-3% of the composition.

wherein all percentages are percentages by weight and wherein the total weight is 100%.

In another embodiment, the composition further comprises a film coat.

In a preferred embodiment, the composition of the invention comprises:

(1) adagrasib at about 33.3% percent of the composition;

(2) microcrystalline cellulose at about 51.2% of the composition;

(3) mannitol at about 10.0% of the composition;

(4) crospovidone at about 3.0% of the composition;

(5) colloidal silicon dioxide at about 1.0% of the composition; and (6) magnesium stearate at about 1.5% of the composition, wherein all percentages are percentages by weight and wherein the total weight is 100%.

In another embodiment, the solid pharmaceutical composition is prepared by a process which comprises the steps of:

(a) pre-blending, wherein diluents, a glidant, and adagrasib are blended together;

(b) de-lumping the components of step (a) using a screening mill;

(c) blending the components of step (b) with a disintegrant, and a glidant;

(d) lubricating by adding a lubricant to the components of step (c);

(e) performing a dry granulation of the components of step (d) using a roller compactor, producing a granulated blend;

(f) blending a diluent, a disintegrant and a glidant with the granulated blend of step (e);

(g) lubricating by adding a lubricant to the components of step (f) to produce a lubricated blend;

(h) performing compression by charging the lubricated blend of step (g) to a rotary tablet press and compressing the lubricated blend into tablet cores; and (i) performing film coating by charging the core tablets of step (h) into a pan coater and adding a film coating agent.

One or more pharmaceutically acceptable excipients (or combinations thereof) may be included as intragranular material, i.e., included prior to conducting dry granulation;

and/or such excipients may be added as extra-granular material to the dry granulation product, i.e., added after the dry granulation product has been dried.

In yet another embodiment, the invention is directed to a method of making a solid pharmaceutical composition comprising adagrasib or a salt thereof, wherein said solid pharmaceutical composition is made by dry granulation.

In one embodiment, the method comprises the steps of:

(a) pre-blending, wherein diluents, a glidant, and adagrasib are blended together;
(b) de-lumping the components of step (a) using a screening mill;
(c) blending the components of step (b) with a disintegrant, and a glidant;
(d) performing an intra-granular lubrication by adding a lubricant to the components of step (c);
(e) performing a dry granulation of the components of step (d) using a roller compactor, producing a granulated blend;
(f) blending a diluent, a disintegrant and a glidant with the granulated blend of step (e);
(g) performing an extra-granular lubrication by adding a lubricant to the components of step (f) to produce a lubricated blend;
(h) performing compression by charging the lubricated blend of step (g) to a rotary tablet press and compressing the lubricated blend into tablet cores; and
(i) adding a film coating to the tablet cores of step (h).

The pharmaceutical compositions provided herein can further include one or more pharmaceutically acceptable additives such as a suspending agent, a flavoring agent, a sweetening agent, a dispersing agent, a surfactant, a colorant, a solubilizer, a moistening agent, a plasticizer, a stabilizer, a penetration enhancer, an anti-foaming agent, an antioxidant, an preservative, or a mixture thereof.

In another embodiment, the invention is directed to a method of treating cancer in a subject in need thereof, comprising administering to the subject a therapeutically effective amount of the solid pharmaceutical composition of the present invention. In one embodiment, the therapeutically effective amount is at least, or about, 600 mg of adagrasib. In one embodiment, the cancer is a KRas G12C-associated cancer. In one embodiment, the KRas G12C-associated cancer is lung cancer. In one embodiment, the solid pharmaceutical composition is a tablet.

Also provided herein are methods for treating cancer in a subject in need thereof, the method comprising (a) determining that cancer is associated with a KRas G12C mutation (e.g., a KRas G12C-associated cancer) (e.g., as determined using a regulatory agency-approved, e.g., FDA-approved, assay or kit); and (b) administering to the patient a therapeutically effective amount of the solid pharmaceutical composition of the present invention. In one embodiment, the solid pharmaceutical composition is a tablet.

In one embodiment, the provided methods of treating cancer cause fewer side effects in the subject than side effects associated with administering a capsule composition of the same amount of adagrasib.

It will be understood, however, that the specific dose level and frequency of dosage for any particular patient may be varied and will depend upon a variety of factors including, for example, the activity of the specific polymorph employed, the metabolic stability and length of action of that polymorph, the age, body weight, general health, sex, diet, mode and time of administration, rate of excretion, drug combination, and the severity of the patient's condition.

The pharmaceutical compositions provided herein can be combined with other compounds having related utilities to treat or prevent cancer. In many instances, administration of the subject pharmaceutical compositions in conjunction with these alternative agents enhances the efficacy of such agents. Accordingly, in some instances, the present pharmaceutical compositions, when combined or administered in combination with, e.g., anti-cancer agents, can be used in dosages which are less than the expected amounts when used alone, or less than the calculated amounts for combination therapy.

High drug load formulations containing greater than 50% drug loading with and without Mannitol were successfully evaluated for their processability, in vitro dissolution and bioavailability in preclinical species (dog model). Formulations up to 67% drug loading were successfully evaluated and it was observed that the amount of Mannitol impacts both processability and bioavailability. It was found that reduction of mannitol w/w % from 10% w/w to 5% w/w and 0% w/w increases bioavailability of the drug and improves processability.

EXAMPLES OF THE INVENTION

The following Examples illustrate the invention.

Example 1: Adagrasib Formulations

This example illustrates an adagrasib tablet formulation, which was made and tested for bioavailability and food effect.

The tablet is an immediate release (IR) film-coated tablet for oral administration. The dosage strength of each tablet is 200 mg or 300 mg, or 400 mg or 600 mg active (adagrasib). The qualitative and quantitative composition per unit of drug product is illustrated in Tables 1-9. No overages are used in the product.

TABLE 1

Drug Product, 200 mg (33% (w/w)), Qualitative and Quantitative Unit Composition

| Component | Quantity per Tablet (mg) | Weight % per Tablet | Function |
|---|---|---|---|
| Adagrasib Drug Substance[a] | 200 | 33.33 | Drug Substance |
| Microcrystalline Cellulose[b] | 307 | 51.17 | Diluent |
| Mannitol | 60 | 10 | Diluent |
| Crospovidone | 18 | 3 | Disintegrant |
| Colloidal Silicon Dioxide | 6 | 1 | Glidant |
| Magnesium Stearate[c] | 9 | 1.5 | Lubricant |
| Core Tablet Weight | 600 | 100 | |
| Film Coat Agent | 18-30 | 3-5 | Film Coat |
| Total Tablet Weight | 618-630 | 103-105 | |

TABLE 2

Drug Product, 300-600 mg (50-67% (w/w)), Qualitative and Quantitative Unit Composition

| Component | Quantity per Tablet (mg) | Weight % per Tablet | Function |
|---|---|---|---|
| Adagrasib Drug Substance | 300-600 | 50-67 | Drug Substance |
| Microcrystalline Cellulose | 120-360 | 20-45 | Diluent |
| Mannitol | 0-100 | 0-10 | Diluent |

TABLE 2-continued

| Drug Product, 300-600 mg (50-67% (w/w)), Qualitative and Quantitative Unit Composition | | | |
|---|---|---|---|
| Component | Quantity per Tablet (mg) | Weight % per Tablet | Function |
| Crospovidone | 10-45 | 2-5 | Disintegrant |
| Colloidal Silicon Dioxide | 3-18 | 0.5-2 | Glidant |
| Magnesium Stearate[d] | 6-27 | 1-3 | Lubricant |
| Core Tablet Weight | 450-900 | 100 | |
| Film Coat Agent | 10-54 | 2-6 | Film Coat |
| Total Tablet Weight | 460-954 | 102-106 | |

TABLE 3

| Drug Product, 300 mg (50% (w/w)), Qualitative and Quantitative Unit Composition | | | |
|---|---|---|---|
| Component | Quantity per Tablet (mg) | Weight % per Tablet | Function |
| Adagrasib Drug Substance | 300 | 50 | Drug Substance |
| Microcrystalline Cellulose | 192 | 32 | Diluent |
| Mannitol | 60 | 10 | Diluent |
| Crospovidone | 30 | 5 | Disintegrant |
| Colloidal Silicon Dioxide | 6 | 1 | Glidant |
| Magnesium Stearate[e] | 12 | 2 | Lubricant |
| Core Tablet Weight | 600 | 100 | |
| Film Coat Agent | 18 | 3 | Film Coat |
| Total Tablet Weight | 618 | 103 | |

TABLE 4

| Drug Product, 400 mg (50% (w/w)), Qualitative and Quantitative Unit Composition | | | |
|---|---|---|---|
| Component | Quantity per Tablet (mg) | Weight % per Tablet | Function |
| Adagrasib Drug Substance | 400 | 50 | Drug Substance |
| Microcrystalline Cellulose | 256 | 32 | Diluent |
| Mannitol | 80 | 10 | Diluent |
| Crospovidone | 40 | 5 | Disintegrant |
| Colloidal Silicon Dioxide | 8 | 1 | Glidant |
| Magnesium Stearate[f] | 16 | 2 | Lubricant |
| Core Tablet Weight | 800 | 100 | |
| Film Coat Agent | 24 | 3 | Film Coat |
| Total Tablet Weight | 824 | 103 | |

TABLE 5

| Drug Product, 300 mg (50% (w/w)), Qualitative and Quantitative Unit Composition | | | |
|---|---|---|---|
| Component | Quantity per Tablet (mg) | Weight % per Tablet | Function |
| Adagrasib Drug Substance | 300 | 50 | Drug Substance |
| Microcrystalline Cellulose | 222 | 37 | Diluent |
| Mannitol | 30 | 5 | Diluent |
| Crospovidone | 30 | 5 | Disintegrant |
| Colloidal Silicon Dioxide | 6 | 1 | Glidant |

TABLE 5-continued

| Drug Product, 300 mg (50% (w/w)), Qualitative and Quantitative Unit Composition | | | |
|---|---|---|---|
| Component | Quantity per Tablet (mg) | Weight % per Tablet | Function |
| Magnesium Stearate[g] | 12 | 2 | Lubricant |
| Core Tablet Weight | 600 | 100 | |
| Film Coat Agent | 18 | 3 | Film Coat |
| Total Tablet Weight | 618 | 103 | |

TABLE 6

| Drug Product, 400 mg (50% (w/w)), Qualitative and Quantitative Unit Composition | | | |
|---|---|---|---|
| Component | Quantity per Tablet (mg) | Weight % per Tablet | Function |
| Adagrasib Drug Substance | 400 | 50 | Drug Substance |
| Microcrystalline Cellulose | 296 | 37 | Diluent |
| Mannitol | 40 | 5 | Diluent |
| Crospovidone | 40 | 5 | Disintegrant |
| Colloidal Silicon Dioxide | 8 | 1 | Glidant |
| Magnesium Stearate[h] | 16 | 2 | Lubricant |
| Core Tablet Weight | 800 | 100 | |
| Film Coat Agent | 24 | 3 | Film Coat |
| Total Tablet Weight | 824 | 103 | |

TABLE 7

| Drug Product, 300 mg (57.14% (w/w)), Qualitative and Quantitative Unit Composition | | | |
|---|---|---|---|
| Component | Quantity per Tablet (mg) | Weight % per Tablet | Function |
| Adagrasib Drug Substance | 300 | 57.14 | Drug Substance |
| Microcrystalline Cellulose | 190.75 | 36.36 | Diluent |
| Mannitol | 0 | 0 | Diluent |
| Crospovidone | 15.75 | 3 | Disintegrant |
| Colloidal Silicon Dioxide | 10.5 | 2 | Glidant |
| Magnesium Stearate[i] | 8 | 1.5 | Lubricant |
| Core Tablet Weight | 525 | 100 | |
| Film Coat Agent | 15.75 | 3 | Film Coat |
| Total Tablet Weight | 540.75 | 103 | |

TABLE 8

| Drug Product, 400 mg (57.14% (w/w)), Qualitative and Quantitative Unit Composition | | | |
|---|---|---|---|
| Component | Quantity per Tablet (mg) | Weight % per Tablet | Function |
| Adagrasib Drug Substance | 400 | 57.14 | Drug Substance |
| Microcrystalline Cellulose | 254.5 | 36.36 | Diluent |
| Mannitol | 0 | 0 | Diluent |
| Crospovidone | 21 | 3 | Disintegrant |
| Colloidal Silicon Dioxide | 14 | 2 | Glidant |
| Magnesium Stearate[j] | 10.5 | 1.5 | Lubricant |
| Core Tablet Weight | 700 | 100 | |
| Film Coat Agent | 21 | 3 | Film Coat |
| Total Tablet Weight | 721 | 103 | |

TABLE 9

| Drug Product, 600 mg (66.67% (w/w)), Qualitative and Quantitative Unit Composition | | | |
|---|---|---|---|
| Component | Quantity per Tablet (mg) | Weight % per Tablet | Function |
| Adagrasib Drug Substance | 600 | 66.67 | Drug Substance |
| Microcrystalline Cellulose | 241.47 | 26.83 | Diluent |
| Mannitol | 0 | 0 | Diluent |
| Crospovidone | 27 | 3 | Disintegrant |
| Colloidal Silicon Dioxide | 18 | 2 | Glidant |
| Magnesium Stearate[k] | 13.5 | 1.5 | Lubricant |
| Core Tablet Weight | 900 | 100 | |
| Film Coat Agent | 27 | 3 | Film Coat |
| Total Tablet Weight | 927 | 103 | |

Example 2: Pharmacokinetics

A first objective of the study was to investigate the relative bioavailability (BA) and pharmacokinetic (PK) profiles of MRTX849 (i.e., adagrasib) in capsule and tablet formulations following single-dose oral administration in healthy subjects under fasted conditions, to evaluate the effect of food on the PK profile of MRTX849 in tablet formulation following single-dose oral administration in healthy subjects, and to evaluate side effects.

The secondary objective of the study was to investigate the safety and tolerability, including incidence of adverse events (side effects), of a single-dose oral administration of capsule and tablet formulations of MRTX849 in healthy subjects under fasted and fed conditions.

Finally, the exploratory objectives of the study were to investigate the PK profiles of potential MRTX849 metabolites following single-dose oral administration of MRTX849 capsule and tablet formulations in healthy subjects under fasted and fed conditions.

Methodology

This study was a phase 1, randomized, open-label, 2×2 crossover trial in healthy subjects and consisted of 2 parts. In part 1, 38 subjects were enrolled and received a single oral dose of adagrasib 600 mg administered as capsule (Reference [R]) or tablet (Test [T]) formulations under fasting conditions in 1 of the 2 randomized treatment sequences (RT or TR).

In part 2, 20 subjects were enrolled and received a 600 mg dose of adagrasib as three tablets of 200 mg adagrasib under fasting (R) or fed (a high-fat, high-calorie meal; T) conditions in 1 of the 2 randomized treatment sequences (RT or TR). Treatments within the sequence were separated by a washout period of 9 to 12 days. Serial pharmacokinetic (PK) blood samples were collected from pre-dose through 168 hours post-dose. Noncompartmental analysis was conducted to derive the primary PK parameters ($C_{max}$, $AUC_{last}$, and $AUC_{\infty}$). Log-transformed PK parameters were analyzed by a mixed effect model which included treatment, period, and sequence as fixed effects and subject nested within sequence as a random effect. For each PK parameter, a point estimate and its associated 90% confidence interval (CI) were constructed for the treatment difference between T and R treatments (i.e., tablet vs capsule, fed vs fasted) and this difference and its 90% CI were exponentiated to obtain the ratio of geometric least-squares mean (GLSM) and its 90% CI.

Results

In part 1, 35 subjects provided evaluable PK data for statistical analysis. The relative BA of the tablet formulation was approximately 89% compared to the capsule formulation. The GLSM ratios (90% CIs) for $C_{max}$, $AUC_{last}$, and $AUC_{\infty}$ were 86.47% (77.53%-96.43%), 88.82% (79.87%-98.78%), and 88.90% (79.98%-98.81%), respectively.

In part 2, 15 subjects provided evaluable PK data for statistical analysis. Food increased $C_{max}$ and AUC of the tablet formulation by approximately 20% and 38%, respectively. The GLSM ratios (90% CIs) for $C_{max}$, $AUC_{last}$, and $AUC_{\infty}$ were 120.33% (95.27%-151.99%), 137.64% (113.86%-166.37%), and 137.53% (113.85%-166.12%), respectively. Adagrasib was generally well tolerated, with gastrointestinal (GI) disorders most frequently reported. The frequency of diarrhea, nausea, and vomiting was lower for the tablet vs capsule formulations (19.4% vs 35.1%, 13.9% vs 32.4%, and 0% vs 2.7%, respectively) and for the tablet fed vs fasted conditions (12.5% vs 47.4%, 6.3% vs 36.8%, and 0% vs 21.1%, respectively).

Table 10 shows results of a bioavailability study of a single dose of 600 mg adagrasib mixed form capsules (reference) and mixed form tablets (Test 1) under Fasted Conditions.

TABLE 10

Statistical Analysis of MRTX849 Primary Pharmacokinetic Endpoints to Assess Relative Bioavailability of a Single Dose of 600 mg MRTX849 Mixed Form Capsules (Reference) and Mixed Form Tablets (Test 1) under Fasted Conditions

| | | | | | | 90% for Ration % | | Within-subject CV |
|---|---|---|---|---|---|---|---|---|
| Parameter | Treatment | n | GLSM | Comparison | Ratio | Lower | Upper | (%) |
| $AUC_{\infty}$ (h*ng/mL) | R | 23 | 12927.42 | | | | | |
| | T1 | 23 | 12315.56 | T1 vs R | 95.27 | 84.93 | 106.86 | 22.9 |
| $AUC_{last}$ (h*ng/mL) | R | 23 | 12886.28 | | | | | |
| | T1 | 23 | 12272.80 | T1 vs R | 95.24 | 84.87 | 106.87 | 23.0 |

TABLE 10-continued

Statistical Analysis of MRTX849 Primary Pharmacokinetic Endpoints to Assess Relative Bioavailability of a Single Dose of 600 mg MRTX849 Mixed Form Capsules (Reference) and Mixed Form Tablets (Test 1) under Fasted Conditions

| Parameter | Treatment | n | GLSM | Comparison | Ratio | 90% for Ration % Lower | 90% for Ration % Upper | Within-subject CV (%) |
|---|---|---|---|---|---|---|---|---|
| $C_{max}$ (ng/mL) | R | 23 | 514.13 | | | | | |
| | T1 | 23 | 495.02 | T1 vs R | 96.28 | 86.59 | 107.06 | 21.1 |

$AUC_{\infty}$ = area under the plasma concentration-time curve from time zero to infinity;
$AUC_{last}$ = area under the curve from time zero to time of last measurable concentration;
CI = confidence interval;
$C_{max}$ = maximum (peak) plasma drug concentration;
GLSM = geometric least squares mean;
ln = natural logarithm;
n = number of subject with valid observations;
R: 600 mg MRTX849 Mixed Form capsules (reference)
T1: 600 mg MRTX849 Mixed Form tablets (intermediate test1)
Model: ln(PK Parameter) = Sequence + Treatment(R and T1) + Random Error, with Subject fitted as a random effect.
Degrees of Freedom method = KR
For each model, data for the reference and test drugs were included exclusively.
The ratio and corresponding confidence limits (expressed as percentages) were back-transformed from the difference and confidence limits calculated on the log scale.
Only subjects with valid PK parameters for both treatments were included for the statistical analysis.

Table 10 shows that the relative BA of the Mixed Form tablet formulation was approximately 5% lower compared to the Mixed Form capsule formulation. Mixed Form capsules and tablets include a mixture of Form 1 and Form 2 crystalline forms of adagrasib. Bioequivalence was demonstrated for Mixed Form tablets versus Mixed Form capsules and Form 2 capsules versus Mixed Form capsules as the 90% CI for the GLSM ratios of MRTX849 primary PK parameters ($C_{max}$, $AUC_{last}$, and $AUC_{\infty}$) were within the regulatory BE limits of 80.00% to 125.00%. Within-subject variability was less than 25%.

Table 11 shows summary PK parameters for adagrasib in plasma.

TABLE 11

Summary of MRTX849 Pharmacokinetic Parameters After Administration of a Single Dose of 600 mg MRTX849 Mixed Form Capsules (Reference), Mixed Form Tablets (Test 1), and Form 2 Capsules (Test 2) under Fasted Conditions

| Parameter | 600 mg MRTX849 Mixed Form Capsules, Fasted (Reference) (N = 23) | 600 mg MRTX849 Mixed Form Tablets, Fasted (Intermediate Test 1) (N = 24) | 600 mg MRTX849 Form 2 Capsules, Fasted (Intermediate Test 2) (N = 23) |
|---|---|---|---|
| $AUC_{last}$ (h*ng/ml) | 12920 (30.7) [23] | 12550 (42.0) [24] | 12680 (40.9) [22] |
| $AUC_{\infty}$ (h*ng/ml) | 12960 (30.7) [23] | 12590 (41.9) [24] | 12730 (40.8) [22] |
| $C_{max}$ (ng/ml) | 516 (28.5) [23] | 502 (40.3) [24] | 533 (40.5) [22] |

TABLE 11-continued

Summary of MRTX849 Pharmacokinetic Parameters After Administration of a Single Dose of 600 mg MRTX849 Mixed Form Capsules (Reference), Mixed Form Tablets (Test 1), and Form 2 Capsules (Test 2) under Fasted Conditions

| Parameter | 600 mg MRTX849 Mixed Form Capsules, Fasted (Reference) (N = 23) | 600 mg MRTX849 Mixed Form Tablets, Fasted (Intermediate Test 1) (N = 24) | 600 mg MRTX849 Form 2 Capsules, Fasted (Intermediate Test 2) (N = 23) |
|---|---|---|---|
| CL/F (L/h) | 46.3 (30.7) [23] | 47.7 (41.9) [24] | 47.1 (40.8) [22] |
| $t_{max}$ (h) | 6.07 (6.00-12.02) [23] | 6.07 (4.02-12.00) [24] | 6.02 (6.00-8.02) [22] |
| $t_{1/2}$ (h) | 16.9 (18.0) [23] | 16.8 (18.8) [24] | 16.7 (17.5) [22] |
| $V_Z$/F (L) | 1113 (33.3) [23] | 1136 (39.9) [24] | 1117 (44.3) [22] |

$AUC_{\infty}$ = area under the plasma concentration-time curve from time zero to infinity;
$AUC_{last}$ = area under the concentration-time curve from time 0 to the time of the last quantifiable concentration ($t_{last}$);
CL/F = apparent total clearance of the drug from plasma after oral administration;
$C_{max}$ = maximum (peak) plasma drug concentration;
CV = coefficient of variation (%);
n = number of subjects with valid observations;
N = number of subjects;
NC = not calculated;
$t_{1/2}$ = elimination half-life;
$t_{max}$ = time to reach maximum (peak) plasma concentration following drug administration;
$V_Z$/F = apparent volume of distribution during terminal phase after non-intravenous administration;
Geometric mean (CV) [n] statistics presented; for $t_{max}$, median (min-max) [n] statistics presented; for $t_{1/2}$, arithmetic mean (arithmetic CV) statistics presented.

Table 12 also shows summary PK parameters for adagrasib in plasma.

TABLE 12

Summary of MRTX849 Pharmacokinetic Parameters After Administration of a Single Dose of 600 mg MRTX849 Mixed Form Capsules (Reference) and Form 2 Tablets (Test) under Fasted Conditions

| Parameter | 600 mg MRTX849 Mixed Form Capsules, Fasted (Reference) (N = 37) | 600 mg MRTX849 Form 2 Tablets, Fasted (Test) (N = 36) |
|---|---|---|
| $AUC_{last}$ (h*ng/ml) | 14020 (58.5) [36] | 12530 (62.9) [36] |
| $AUC_{\infty}$ (h*ng/mL) | 14070 (58.3) [36] | 12590 (62.6) [36] |
| $C_{max}$ (ng/ml) | 556 (49.0) [36] | 486 (54.6) [36] |
| CL/F (L/h) | 42.7 (58.3) [36] | 47.7 (62.6) [36] |
| $t_{max}$ (h) | 7.50 (4.05-12.00) [36] | 6.07 (4.03-12.00) [36] |
| $t_{1/2}$ (h) | 17.0 (17.7) [36] | 17.2 (16.9) [36] |
| $V_Z/F$ (L) | 1030 (52.0) [36] | 1166 (55.7) [36] |

$AUC_{\infty}$ = area under the plasma concentration-time curve from time zero to infinity;
$AUC_{last}$ = area under the concentration-time curve from time 0 to the time of the last quantifiable concentration ($t_{last}$);
CL/F = apparent total clearance of the drug from plasma after oral administration;
$C_{max}$ = maximum (peak) plasma drug concentration;
CV = coefficient of variation (%);
n = number of subjects with valid observations;
N = number of subjects;
NC = not calculated;
$t_{1/2}$ = elimination half-life;
$t_{max}$ = time to reach maximum (peak) plasma concentration following drug administration;
$V_Z/F$ = apparent volume of distribution during terminal phase after non-intravenous administration;
Geometric mean (CV) [n] statistics presented; for $t_{max}$, median (min-max) [n] statistics presented; for $t_{1/2}$, arithmetic mean (arithmetic CV) statistics presented.

Table 13 presents statistical analysis for the assessment of the relative BA of 600 mg MRTX849 Mixed Form capsules (reference) and Form 2 tablets (test) based on the primary PK parameters of MRTX849.

TABLE 13

Statistical Analysis of MRTX849 Primary Pharmacokinetic Endpoints to Assess Relative Bioavailability of a Single Dose of 600 mg MRTX849 Mixed Form Capsules (Reference) and Form 2 Tablets (Test) under Fasted Conditions

| Parameter | Treatment | n | GLSM | Ratio (%) GLSM (T vs R) | 90% CI For the Ratio (%) Lower | Upper | Within-subject CV (%) |
|---|---|---|---|---|---|---|---|
| $AUC_{\infty}$ (h*ng/mL) | R | 35 | 14154.12 | | | | |
| | T | 35 | 12582.72 | 88.90 | 79.98 | 98.81 | 26.6 |
| $AUC_{last}$ (h*ng/mL) | R | 35 | 14102.37 | | | | |
| | T | 35 | 12526.36 | 88.82 | 79.87 | 98.78 | 26.7 |
| $C_{max}$ (ng/mL) | R | 35 | 558.67 | | | | |
| | T | 35 | 483.07 | 86.47 | 77.53 | 96.43 | 27.4 |

$AUC_{\infty}$ = area under the plasma concentration-time curve from time zero to infinity;
$AUC_{last}$ = area under the plasma concentration-time curve from time zero to time of last measurable concentration;
CI = confidence interval;
$C_{max}$ = maximum (peak) plasma drug concentration;
GLSM = geometric least squares mean;
ln = natural logarithm;
n = number of subjects with valid observations;
R: 600 mg MRTX849 Mixed Form capsules (reference)
T: 600 mg MRTX849 Form 2 tablets (test)
Model: ln(PK Parameter) = Sequence + Period + Treatment + Random Error, with Subject fitted as a random effect.
Degrees of Freedom method = KR
The ratio and corresponding confidence limits (expressed as percentages) were back-transformed from the difference and confidence limits calculated on the log scale.

Results showed that relative BA of Form 2 tablets was approximately 89% compared to the Mixed Form capsules based on AUCs (Table 11). However, BE between Form 2 tablets and Mixed Form capsules was not met as the 90% CIs for the GLSM ratios for $C_{max}$, $AUC_{last}$, and $AUC_{\infty}$ were not contained within the regulatory BE limits of 80.00% to 125.00%. While the upper boundary of the 90% CI for the primary PK parameters was within the BE limit of 125.00%, the lower boundary of the 90% CI for $C_{max}$, $AUC_{last}$, and $AUC_{\infty}$ (77.53%, 79.87%, and 79.98%, respectively) was slightly below the BE limit of 80.00%.

Food effect was investigated as part of the study.

Eligible subjects were randomized to 1 of 2 treatment sequences. For Periods 1 and 2, eligible subjects were admitted into the clinical research unit (CRU) on Day-1 and confined to the CRU until discharge on Day 8. A single 600-mg dose of MRTX849 (Form 2 tablets) was to be administered either under fasting conditions or with a high-fat, high-calorie breakfast on Day 1 of each of Periods 1 and 2. The dose of MRTX849 was determined based on the preliminary results from Part 1. Each period included serial blood collections obtained from predose through 168 hours postdose for analysis of plasma concentrations of MRTX849 (and metabolites, if applicable). A washout period of 9 to 12 days after dose administration in Period 1 was required. A follow-up phone call was scheduled between 2 and 5 days, inclusive, after discharge from Period 2.

Results showed that the high-fat, high-calorie meal increased MRTX849 Form 2 tablets' $C_{max}$ and AUC by approximately 20% and 38%, respectively (Table 14). The efficacy and safety profiles of MRTX849 in patients are being characterized using Mixed Form capsules under fasting conditions. Accounting for the relative BA of Form 2 tablets compared to Mixed Form capsules, Form 2 tablets under fed conditions are expected to result in approximately 4% higher $C_{max}$ and 22% higher AUC compared to the Mixed Form capsules under fasted conditions. Furthermore, Form 2 tablets under fed conditions showed lower between-subject variability than under fasted conditions which may result in less variability in clinical response in patients. Therefore, the effect of food on MRTX849 Form 2 tablet is not considered clinically meaningful.

TABLE 14

Statistical Analysis of MRTX849 Primary Pharmacokinetic Endpoints to Assess the Effect of Food on a Single Dose of 600 mg MRTX849 Form 2 Tablets

| Parameter | Treatment | n | GLSM | Ratio (%) GLSM (T:R) | 90% CI For the Ratio (%) Lower | Upper | Within-subject CV (%) |
|---|---|---|---|---|---|---|---|
| $AUC_\infty$ (h*ng/mL) | R | 15 | 14113.65 | | | | |
| | T | 15 | 19409.83 | 137.53 | 113.85 | 166.12 | 29.8 |
| $AUC_{last}$ (h*ng/mL) | R | 15 | 14055.46 | | | | |
| | T | 15 | 19345.25 | 137.64 | 113.86 | 166.37 | 29.9 |
| $C_{max}$ (ng/mL) | R | 15 | 527.43 | | | | |
| | T | 15 | 634.67 | 120.33 | 95.27 | 151.99 | 37.2 |

$AUC_\infty$ = area under the plasma concentration-time curve from time zero to infinity;
$AUC_{last}$ = area under the plasma concentration-time curve from time zero to time of last measurable concentration;
CI = confidence interval;
$C_{max}$ = maximum (peak) plasma drug concentration;
GLSM = geometric least squares mean;
ln = natural logarithm;
n = number of subjects with valid observations;
R: 600 mg MRTX849 Form 2 tablets, fasted condition (reference)
T: 600 mg MRTX849 Form 2 tablets, fed condition (test)
Model: ln(PK Parameter) = Sequence + Period + Treatment + Random Error, with Subject fitted as a random effect
The ratio and corresponding confidence limits (expressed as percentages) were back-transformed from the difference and confidence limits calculated on the log scale.
Only subjects with data for both treatments (fasted and fed) are included in the analysis.

Side Effects

The frequency of gastrointestinal disorders, in particular diarrhea, nausea, and vomiting, appeared to be lower during tablet dosing compared to during capsule dosing. Also, the frequency of gastrointestinal disorders, particularly diarrhea, nausea, abdominal pain, and vomiting, appeared to be lower when tablets were taken with food compared to fasted conditions.

A summary of side effects is displayed in Table 15.

TABLE 15

Summary of Treatment -emergent Adverse Events by System Organ Class and Preferred Term

| System Organ Class Preferred Term | Part 1 MF capsules (R) (N = 23) nS (%) | Part 1 MF tablets (T1) (N = 24) nS (%) | Part 1 F2 capsules (T2) (N = 23) nS (%) | Part 2 MF capsules (R) (N = 37) nS (%) | Part 2 F2 tablets (T) (N = 36) nS (%) | Part 3 F2 tablets (fasted; R) (N = 19) nS (%) | Part 3 F2 tablets (fed; T) (N = 16) nS (%) | Overall (N = 82) nS (%) |
|---|---|---|---|---|---|---|---|---|
| Overall | 11 (47.8%) | 9 (37.5%) | 15 (65.2%) | 21 (56.8%) | 8 (22.2%) | 10 (52.6%) | 4 (25.0%) | 53 (64.6%) |
| Gastrointestinal disorders | 11 (47.8%) | 8 (33.3%) | 12 (52.2%) | 20 (54.1%) | 8 (22.2%) | 10 (52.6%) | 3 (18.8%) | 48 (58.5%) |
| Diarrhoea | 10 (43.5%) | 7 (29.2%) | 5 (21.7%) | 13 (35.1%) | 7 (19.4%) | 9 (47.4%) | 2 (12.5%) | 37 (45.1%) |
| Nausea | 6 (26.1%) | 4 (16.7%) | 9 (39.1%) | 12 (32.4%) | 5 (13.9%) | 7 (36.8%) | 1 (6.3%) | 34 (41.5%) |
| Abdominal pain | 1 (4.3%) | 1 (4.2%) | 2 (8.7%) | 2 (5.4%) | 2 (5.6%) | 1 (5.3%) | — | 8 (9.8%) |
| Vomiting | — | — | 1 (4.3%) | 1 (2.7%) | — | 4 (21.1%) | — | 6 (7.3%) |
| Abdominal discomfort | — | — | — | 2 (5.4%) | 1 (2.8%) | — | — | 3 (3.7%) |
| Abdominal pain lower | — | — | — | — | — | 1 (5.3%) | — | 1 (1.2%) |
| Dry mouth | — | — | 1 (4.3%) | — | — | — | — | 1 (1.2%) |
| Eructation | — | — | — | 1 (2.7%) | — | — | — | 1 (1.2%) |
| Regurgitation | 1 (4.3%) | — | — | — | — | — | — | 1 (1.2%) |
| Retching | 1 (4.3%) | — | — | — | — | — | — | 1 (1.2%) |
| Salivary hypersecretion | — | — | — | 1 (2.7%) | — | — | — | 1 (1.2%) |
| Nervous system disorders | 6 (26.1%) | 2 (8.3%) | 3 (13.0%) | 1 (2.7%) | — | 3 (15.8%) | — | 11 (13.4%) |
| Headache | 4 (17.4%) | 1 (4.2%) | 2 (8.7%) | 1 (2.7%) | — | 1 (5.3%) | — | 7 (8.5%) |
| Dizziness | 1 (4.3%) | — | 1 (4.3%) | — | — | 2 (10.5%) | — | 3 (3.7%) |
| Presyncope | 2 (8.7%) | — | — | — | — | — | — | 2 (2.4%) |
| Paraesthesia | — | 1 (4.2%) | — | — | — | — | — | 1 (1.2%) |
| Parosmia | — | — | 1 (4.3%) | — | — | — | — | 1 (1.2%) |

F2 = Form 2;
MF = mixed form;
nS = number of subjects with an adverse event;
N = number of subjects;
% = percentage of subjects with valid observations (nS/N x 100)
Adverse events were coded using the Medical Dictionary for Regulatory Activities (MedDRA) Version 23.0
A treatment-emergent adverse event (TEAE) was defined as an adverse event that started during or after dosing, or started prior to dosing and increased in severity after dosing.

Example 3: Tablet Manufacturing Process

This example illustrates an exemplary manufacturing process for an adagrasib tablet.

FIG. 1 describes a manufacturing process flow diagram that may be used to prepare solid formulations of the invention.

Manufacturing Process Description is as follows.

Pre-Blending (Stage 1)

1. Charge portion of microcrystalline cellulose and portion of colloidal silicon dioxide into the blender and blend the components.

Pre-Blending (Stage 2)

2. Charge adagrasib drug substance, portion of microcrystalline cellulose, and mannitol into the same blender and blend the components.

De-Lumping

3. De-lump the components using a conical screening mill.

Intra-Granular Blending

4. Charge portion of crospovidone and portion of colloidal silicon dioxide (0.5% w/w) into the same blender and blend the components.

Intra-Granular Lubrication

5. Charge portion of magnesium stearate into the same blender and blend the components.

Dry Granulation (Roller Compaction)

6. Charge the components from step 9 to a roller compactor connected to an oscillatory mill and granulate the blend.

Extra-Granular Blending

7. Charge portion of microcrystalline cellulose, portion of crospovidone, and portion of colloidal silicon dioxide into the blender containing the granulated blend and blend the components.

Extra-Granular Lubrication

8. Charge portion of magnesium stearate into the blender and blend the components.

Compression

9. Charge the final lubricated blend to a rotary tablet press and compress the blend into tablet cores.

10 Perform dedusting and metal detection of core tablet products.

In-Process Controls

Tablet appearance, weight, and hardness are monitored and controlled during the compression step.

Film Coating

11. Prepare an aqueous suspension of film coat agent and purified water using a mixer and appropriate size vessel.

12. Charge the core tablets into a perforated pan coater, and coat the tablet by spraying the suspension from previous step to 3-4% weight gain.

All publications and patent applications cited in this specification are herein incorporated by reference as if each individual publication or patent application were specifically and individually indicated to be incorporated by reference. Although the foregoing has been described in some detail by way of illustration and example for purposes of clarity of understanding, it will be readily apparent to those of ordinary skill in the art in light of the teachings of the specification that certain changes and modifications may be made thereto without departing from the spirit or scope of the appended claims.

What is claimed is:

1. A tablet formulation for oral administration in a human, comprising:

(1) adagrasib constituting about 30-35% of the tablet formulation;

(2) microcrystalline cellulose constituting about 50-55% of the tablet formulation;

(3) mannitol constituting about 8-10% of the tablet formulation;

(4) crospovidone constituting about 2% to about 5% of the tablet formulation;

(5) colloidal silicon dioxide constituting up to about 0.5-1.5% of the tablet formulation;

and (6) the magnesium stearate constitutes about 1-2% of the tablet formulation, and wherein all percentages are percentages by weight, and wherein an adverse gastrointestinal event occurs in a lower frequency in the human administered the tablet formulation compared to a human administered a capsule formulation with the same amount of adagrasib.

2. The tablet formulation of claim 1, wherein the tablet formulation further comprises a film coat.

3. The tablet formulation of claim 1, wherein:

(1) the adagrasib constitutes about 33.3% of the tablet formulation;

(2) the microcrystalline cellulose constitutes about 51.2% of the tablet formulation;

(3) the mannitol constitutes about 10.0% of the tablet formulation;

(4) the crospovidone constitutes about 3.0% of the tablet formulation;

(5) the colloidal silicon dioxide constitutes about 1.0% of the tablet formulation; and (6) the magnesium stearate constitutes about 1.5% of the tablet formulation.

4. The tablet formulation of claim 1, wherein the adverse gastrointestinal event is nausea.

5. The tablet formulation of claim 1, wherein the adverse gastrointestinal event is vomiting.

6. The tablet formulation of claim 1, wherein the adverse gastrointestinal event is diarrhea.

7. The tablet formulation of claim 1, wherein the amount of adagrasib in the tablet formulation is at least, or about, 200 mg.

8. The tablet formulation of claim 1, wherein the amount of adagrasib in the tablet formulation is at least, or about, 300 mg.

9. The tablet formulation of claim 1, wherein the amount of adagrasib in the tablet formulation is at least, or about, 400 mg.

* * * * *